United States Patent [19]

Miyawaki

[11] Patent Number: 4,850,368

[45] Date of Patent: Jul. 25, 1989

[54] ELECTRONIC BLOOD PRESSURE MEASUREMENT DEVICE AND ITS METHOD OF OPERATION, PERFORMING MINIMAL SQUEEZING OF PATIENT'S ARM

[75] Inventor: Toshinori Miyawaki, Yawata, Japan

[73] Assignee: Omron Tateisi Electronics Co., Kyoto, Japan

[21] Appl. No.: 217,044

[22] Filed: Jul. 7, 1988

Related U.S. Application Data

[63] Continuation of Ser. No. 900,585, Aug. 26, 1986.

[30] Foreign Application Priority Data

Aug. 27, 1985 [JP] Japan .................... 60-189076

[51] Int. Cl.$^4$ .................................... A61B 5/02
[52] U.S. Cl. .................................. 128/680; 128/683
[58] Field of Search ............... 128/680, 683, 687, 672, 128/689, 637, 677

[56] References Cited

U.S. PATENT DOCUMENTS 4,190,886  2/1980  Sherman ........................ 128/900
4,378,807  4/1983  Peterson et al. ................ 128/900

Primary Examiner—Francis Jaworski
Assistant Examiner—George Manuel
Attorney, Agent, or Firm—Wegner & Bretschneider

[57] ABSTRACT

This electronic blood pressure measurement device includes a cuff with pressurization and sensing means, first measuring means for determining systolic, average, and diastolic blood pressures according to the pulse signal, means for computing a blood pressure constant as (systolic - average)/(average - diastolic), second measuring means for determining average and diastolic blood pressures according to the pulse signal, and means for computing systolic blood pressure according to average and diastolic blood pressures and the constant. A control means first operates the first measuring means and then the constant computing means; then stores first pulse characterization data relating to the pulse signal at this time; and then repeatedly: operates the second measuring means and then the means for computing systolic blood pressure; then stores second pulse characterization data relating to the pulse signal at this time; and then compares the first and second stored pulse characterization data and, only if they are significantly different, next returns to the step of operating the first measuring means.

6 Claims, 6 Drawing Sheets

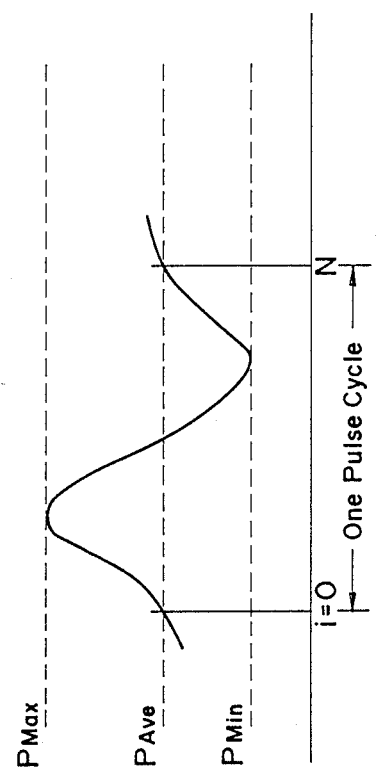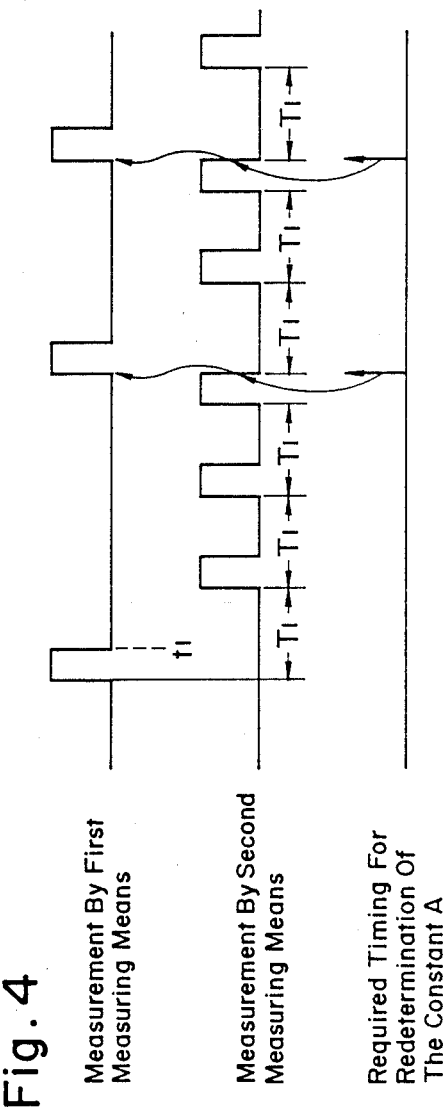

ELECTRONIC BLOOD PRESSURE MEASUREMENT DEVICE AND ITS METHOD OF OPERATION, PERFORMING MINIMAL SQUEEZING OF PATIENT'S ARM

This application is a continuation of U.S. application Ser. No. 900,585, filed Aug. 26. 1986.

BACKGROUND OF THE INVENTION

The present invention relates to an electronic device for measuring the blood pressure of a patient and a method of operation thereof, and more particularly relates to such a device for blood pressure measurement and such a method of operation thereof, of the type adapted to continuous measurement, in which the squeezing of the patient's arm by a cuff incorporated in said device, and the inevitable attendant discomfort and errors due to blood congestion engendered by such squeezing, are minimized.

Generally, in the continuous measurement type of blood pressure measurement device, conventionally a cuff is fitted over the arm of a patient and is inflated by a pressure pump, thereafter being deflated progressively. During these processes, the pressure inside the cuff is measured and a pulse wave signal is obtained therefrom. Typically, in order to provide for continuous blood pressure measurement, the cycles of inflation and deflation of the cuff must be performed repeatedly, and thus the peaks of cuff inflation pressure at which the patient's arm is most squeezed are repeated. However, the problem has existed of pain caused to the patient at such times of high cuff inflation pressure, and furthermore there is a possibility for the patient's arm to become congested with blood at these times, which can adversely affect the blood pressure measurement process and cause erroneous blood pressure measurements.

It is conventionally known that these peaks of cuff inflation pressure are only required for the measurement of the systolic blood pressure while on the other hand the average blood pressure and the diastolic blood pressure are measured at other points in the inflation and deflation cycle for the cuff, at which the pressure in the cuff is relatively lower. Accordingly, in order to overcome such problems and others, there was conceived, and there was specified in Japanese Patent Application Serial No. 59-49750 (1984), which has been laid open to the public as Japanese Patent Laying Open Publication Ser. No. 60-193440 (1985), which it is not intended hereby to admit as prior art to the present patent application except to the extent in any case required by applicable law, and which was applied for and is beneficially owned by the same entity as the entity to whom the present patent application is assigned or is the subject of a duty of assignment, an electronic blood pressure measurement device, comprising: (a) a cuff for being fitted around the arm of a patient; (b) a means for selectively pressurizing said cuff with fluid, so as to squeeze said arm of said patient; (c) a means for selectively draining said fluid from said cuff either at a relatively rapid rate or at a relatively slow rate; (d) a means for sensing the pressure of said fluid in said cuff and for producing an output signal representative thereof; (e) a means for receiving said pressure signal from said cuff pressure sensing means and for generating therefrom a signal representative of the pulse wave of the patient; (f) a first blood pressure measuring means for determining for the patient a systolic blood pressure, an average blood pressure, and a diastolic blood pressure according to said pulse wave signal, during the course of pressurization and gradual evacuation at said relatively slow rate of said cuff; (g) a means for computing the value of a constant as being the ratio of the difference of said systolic blood pressure and said average blood pressure to the difference of said average blood pressure and said diastolic blood pressure, all said blood pressures being as determined by said first blood pressure measuring means; (h) a second blood pressure measuring means for determining for the patient an average blood pressure and a diastolic blood pressure according to said pulse wave signal, during the course of gradual evacuation said relatively slow rate of said cuff; and: (i) a means for computing the value of a systolic blood pressure, according to said average blood pressure and said diastolic blood pressure as determined by said second blood pressure measuring means, and according to the value of said constant as computed by said computing means therefor. Further, this electronic blood pressure measurement device included a control means, which first performed the steps of operating said first blood pressure measuring means so as to determine for the patient a systolic blood pressure, an avverage blood pressure, and a diastolic blood pressure according to the current pulse wave signal, and of operating said constant value computing means so as to determine the value of said constant, and thereafter repeatedly performed the steps of operating said second blood pressure measuring means for determining for the patient an average blood pressure and a diastolic blood pressure according to said pulse wave signal, and of operating said means for computing the value of a systolic blood pressure according to said average blood pressure and said diastolic blood pressure as determined by said second blood pressure measuring means and according to the value of said constant as first determined. Further, at a certain fixed time interval, i.e. after the lapse of a determinate time period, the control means returned to the above described first stage of operating said first blood pressure measuring means and of operating said constant value computing means, so as thereby to determine anew, i.e. to refresh, the value of said constant. There was further disclosed a corresponding method of operation of said electronic blood pressure measurement device. According to this electronic blood pressure measurement device and this method of operation thereof, the squeezing of the patient's arm was reduced, because only in the first above described stage of operation, i.e. during measurement of the systolic blood pressure as well as of the average blood pressure and of the diastolic blood pressure, was it necessary for the pressure in the cuff to be raise to a very high level; during the second above described stage of operation, i.e. during measurement only of the average blood pressure and of the diastolic blood pressure, only light squeezing of the patient's arm was required. Thereby the patient's arm was only required to be relatively severely squeezed, once in every said determinate time period. Accordingly, relatively severe squeezing of the patient's arm, and pain and congestion of the patient's arm due to blood accumulation therein caused thereby, which might unnecessarily disturb the blood pressure measurement process, were reduced.

However, this type of electronic blood pressure measurement device, and the method of operation thereof, although they achieved a certain improvement over prior arts in that the squeezing of the patient's arm was much reduced, were not perfect. In detail, they were subject to the problem that, although from time to time the value of the constant absolutely was needed to be updated by the control device returning to the first stage of operation as described above, because the blood pressure wave form of any individual patient necessarily must change over time and accordingly errors tended to accumulate, nevertheless the most ideal time points for such refreshment of the constant did not necessarily occur at a fixed time interval.

If for example in fact the blood pressure wave form of the patient had not changed significantly, then it was undesirable to return to the first stage of operation, because such a first stage of operation performed relatively severe squeezing of the patient's arm, and accordingly caused pain and some congestion of the patient's arm due to blood accumulation therein, which unnecessarily disturbed the blood pressure measurement process. On the other hand, if in fact the blood pressure wave form of the patient were to change relatively quickly, then it might become desirable to return to the first stage of operation for redetermination of the constant before the complete elapsing of the determinate time period, because otherwise errors in blood pressure measurement might exceed the acceptable levels. The speed of alteration of the blood pressure wave form of the patient cannot be accurately predicted to be a constant in advance, because of variation of the measurement conditions and because of individual differences between patients. Accordingly, the above described electronic blood pressure measurement device, and the method of operation thereof, were subject to the twin problems of either liability to unduly high measurement errors, or of inflating the cuff to a high pressure level more often than actually necessary.

SUMMARY OF THE INVENTION

The inventor of the present invention considered the various problems detailed above in the case when timing of the recalculation of the constant as described above is at a fixed time interval, from the point of view of the desirability of minimizing strong squeezing of the patient's arm while maintaining high measurement accuracy.

Accordingly, it is the primary object of the present invention to provide an electronic blood pressure measurement device of the continuous measurement type, which avoids the problems detailed above.

It is a further object of the present invention to provide such an electronic blood pressure measurement device, which does not strongly squeeze the patient's arm except when necessary.

It is a further object of the present invention to provide such an electronic blood pressure measurement device, which maintains good measurement accuracy.

It is a further object of the present invention to provide such an electronic blood pressure measurement device, which is economical and simple to manufacture.

It is a yet further and concomitant object of the present invention to provide a method of operating such an electronic blood pressure measurement device, which aids with the resolution of the above identified problems, and others.

Generally, it is per se known in the art that a certain correlation exists between the change in the blood pressure wave form and the pulse wave form obtained as the pressure within a cuff around the patient's arm, and it is further known that the blood pressure wave form and the pulse wave form are substantially identical in shape at the time of diastolic blood pressure. In view of such a fast, according to the present invention, the pulse wave form at the time measuring the systolic, the average, and the diastolic blood pressures in a first stage of operation is compared to the pulse wave form at the time of later measuring only the average and the diastolic blood pressures in a second stage of operation in which the systolic blood pressure is calculated based upon said average and diastolic blood pressures and is not independently directly measured; and, as long as said two pulse wave forms are similar within a certain determinate degree, said second stage of operation is repeated, thereby not severely squeezing the patient's arm while still updating the value of the average blood pressure and the value of the diastolic blood pressure. On the other hand, when as will inevitably occur said two pulse wave forms become no longer similar within said certain determinate degree, then said first stage of operation is once repeated, thereby once (but only once) relatively severely squeezing the patient's arm and updating the value of the systolic blood pressure as well as the value of the average blood pressure and the value of the diastolic blood pressure.

FIG. 1 is a schematic block diagram for explaining the main device claim of the present application relating to the electronic blood pressure measurement device of the present invention; and reference numerals in said figure will be included, for explanatory purposes only, in bold in the following statement of the most general device aspect of the present invention. This most general device aspect of the present invention, then, attains the above and other objects by an electronic blood pressure measurement device, comprising: (a) a cuff (1) for being fitted around the arm of a patient; (b) a means (2) for selectively pressurizing said cuff with fluid, so as to squeeze arm of said patient; (c) a means (3) for selectively draining said fluid from said cuff either at a relatively rapid rate or at a relatively slow rate; (d) a means (4) for sensing the pressure of said fluid in said cuff and for producing an output signal representative thereof; (e) a means (5) for receiving said pressure signal from said cuff pressure sensing means and for generating therefrom a signal representative of the pulse wave of the patient; (f) a first blood pressure measuring means (6) for determining for the patient a systolic blood pressure, an average blood pressure, and a diastolic blood pressure according to said pulse wave signal, during the course of pressurization and gradual evacuation at said relatively slow rate of said cuff; (g) a means (7) for computing the value of a constant as being the ratio of the difference of said systolic blood pressure and said average blood pressure to the difference of said average blood pressure and said diastolic blood pressure, all said blood pressures being as determined by said first blood pressure measuring means; (h) a second blood pressure measuring means (8) for determining for the patient an average blood pressure and a diastolic blood pressure according to said pulse wave signal, during the course of gradual evacuation at said relatively slow rate of said cuff; (i) a means for computing the value of a systolic blood pressure, according to said average blood pressure and said diastolic blood pressure as determined by said second blood pressure measuring means, and according to the value of said constant as computed by said computing means therefor; and: (j) a control means (9), for performing the following steps in the specified order starting at step (j1), and further comprising first and second means (10, 11) for storing pulse wave characterization data, means (12) for comparing said pulse wave characterization data, and switching means (13) for selectively actuating the means (b), (c), and (f) through (i) above: (j1) operating, via said switching means, said first blood pressure measuring means so as to determine for the patient a systolic blood pressure, an average blood pressure, and a diastolic blood pressure according to the current pulse wave signal; (j2) operating, via said switching means, said constant value computing means so as to determine the value of said constant as being the ratio of the difference of said systolic blood pressure and said average blood pressure to the difference of said average blood pressure and said diastolic blood pressure, all said blood pressures being as determined by said first blood pressure measuring means during the step (j1); and operating said first means for storing pulse wave characterization data to store pulse wave characterization data relating to the pulse wave at this time; and: (j3) thereafter, repeatedly performing the following steps in the specified order: (j31) operating, via said switching means, said second blood pressure measuring means for determining for the patient an average blood pressure and a diastolic blood pressure according to said pulse wave signal; (j32) operating, via said switchiing means, said means for computing the value of a systolic blood pressure, according to said average blood pressure and said diastolic blood pressure as determined by said second blood pressure measuring means, and according to the value of said constant as computed by said computing means therefor during the step (j2); and operating said second means for storing pulse wave characterization data to store pulse wave characterization data relating to the pulse wave at this time; and: (j33) operating said means for comparing said pulse wave characterization data to compare the pulse wave characterization data stored in said first and said second means for storing pulse wave characterization data; and, only if the result of said comparison indicates that said pulse wave characterization data stored in said first storage means are more distinguished from said pulse wave characterization data stored in said second storage means than a determinate standard, next performing step (j1); and, according to the most general method aspect of the present invention, these and other objects are attained by a method for operating an electric blood pressure measuring device comprising: (a) a cuff for being fitted around the arm of a patient; (b) a means for selectively pressurizing said cuff with fluid, so as to squeeze said arm of said patient; (c) a means for selectively draining said fluid from said cuff either at a relatively rapid rate or at a relatively slow rate; (d) a means for sensing the pressure of said fluid in said cuff and for producing an output signal representative thereof; (e) a means for receiving said pressure signal from said cuff pressure sensing means and for generating therefrom a signal representative of the pulse wave of the patient; (f) a first blood pressure measuring means for determining for the patient a systolic blood pressure, an average blood pressure, and a diastolic blood pressure according to said pulse wave signal, during the course of pressurization and gradual evacuation at said relatively slow rate of said cuff; (h) a second blood pressure measuring means for determining for the patient an average blood pressure and a diastolic blood pressure according to said pulse wave signal, during the course of gradual evacuation at said relatively slow rate of said cuff; wherein the following steps are performed in the specified order starting at step (1): (1) said first blood pressure measuring means is operated so as to determine for the patient a systolic blood pressure, an average blood pressure, and a diastolic blood pressure according to the current pulse wave signal; (2) a value of a constant is determined as being the ratio of the difference of said systolic blood pressure and said average blood pressure to the difference of said average blood pressure and said diastolic blood pressure, all said blood pressures being as determined by said first blood pressure measuring means during the step (1); and first pulse wave characterization data relating to the pulse wave at this time are stored; and: (3) thereafter, repeatedly the following steps in the specified order are performed: (31) said second blood pressure measuring means is operated for determining for the patient an average blood pressure and a diastolic blood pressure according to said pulse wave signal; (32) a systolic blood pressure is computed according to said average blood pressure and said diastolic blood pressure as determined by said second blood pressure measuring means, and according to the value of said constant as determined during the step (2); and second pulse wave characterization data relating to the pulse wave at this time are stored, and: (33) said first and said second stored pulse wave characterization data are compared; and, only if the result of said comparison indicates that said first stored pulse wave characterization data are more distinguished from said second pulse wave characterization data than a determinate standard, next performing step (1).

According to such a device and such an operational method therefor as specified above, since when the blood pressure wave form does not substantially change there is no substantial change in the pulse wave form, therefore at this time the comparison of the first and said second stored pulse wave characterization data produces the result that they are not more distinguished from one another than said determinate standard, and therefore the steps of operating the second blood pressure measuring means and of computing the systolic blood pressure from the thereby measured average blood pressure and the diastolic blood pressure and from the value of said constant are repeated, without unduly squeezing the patient's arm; but the value of the constant is not updated. On the other hand, when a significant change occurs in the blood pressure wave form, a corresponding substantial change occurs in the pulse wave form, and therefore at this time the comparison of the first and said second stored pulse wave characterization data produces the result that they are now definitely more distinguished from one another than said determinate standard, and therefore the step of operating the first blood pressure determining means and of directly measuring the systolic blood pressure as well as the average blood pressure and the diastolic blood pressure is once repeated, thereby unavoidably once relatively severely squeezing the patient's arm. And then the constant is again updated from these new blood pressure measurements; and then the cycle of repeatedly operating the second blood pressure measuring means are again commenced. Hence, in summary, it is seen that the patient's arm is squeezed to a relatively severe amount, when and only when such severe squeezing is absolutely necessary in order to achieve proper blood pressure measurement.

BRIEF DESCRIPTION OF THE DRAWINGS

The present invention will now be described with respect to the preferred embodiments of the device and of the method thereof, and with reference to the illustrative drawings appended hereto, which however are provided for the purposes of explanation and exemplification only, and are not intended to be limitative of the scope of the present invention in any way, since this scope is to be delimited solely by the accompanying claims. With relation to the figures, spatial terms are to be understood as referring only to orientation on the drawing paper, unless otherwise specified; like reference numerals, unless otherwise so specified, denote the same parts and gaps and spaces and so on in the various figures; and:

FIG. 3 is a wave form diagram, showing the process of computing a constant which specifies a pulse wave form, as performed by the device shown in FIG. 2;

FIG. 4 is a time chart showing the operation of this preferred embodiment of the device of the present invention, for explaining the switching over of the measuring system thereof;

DESCRIPTION OF THE PREFERRED EMBODIMENTS

Figure 1:
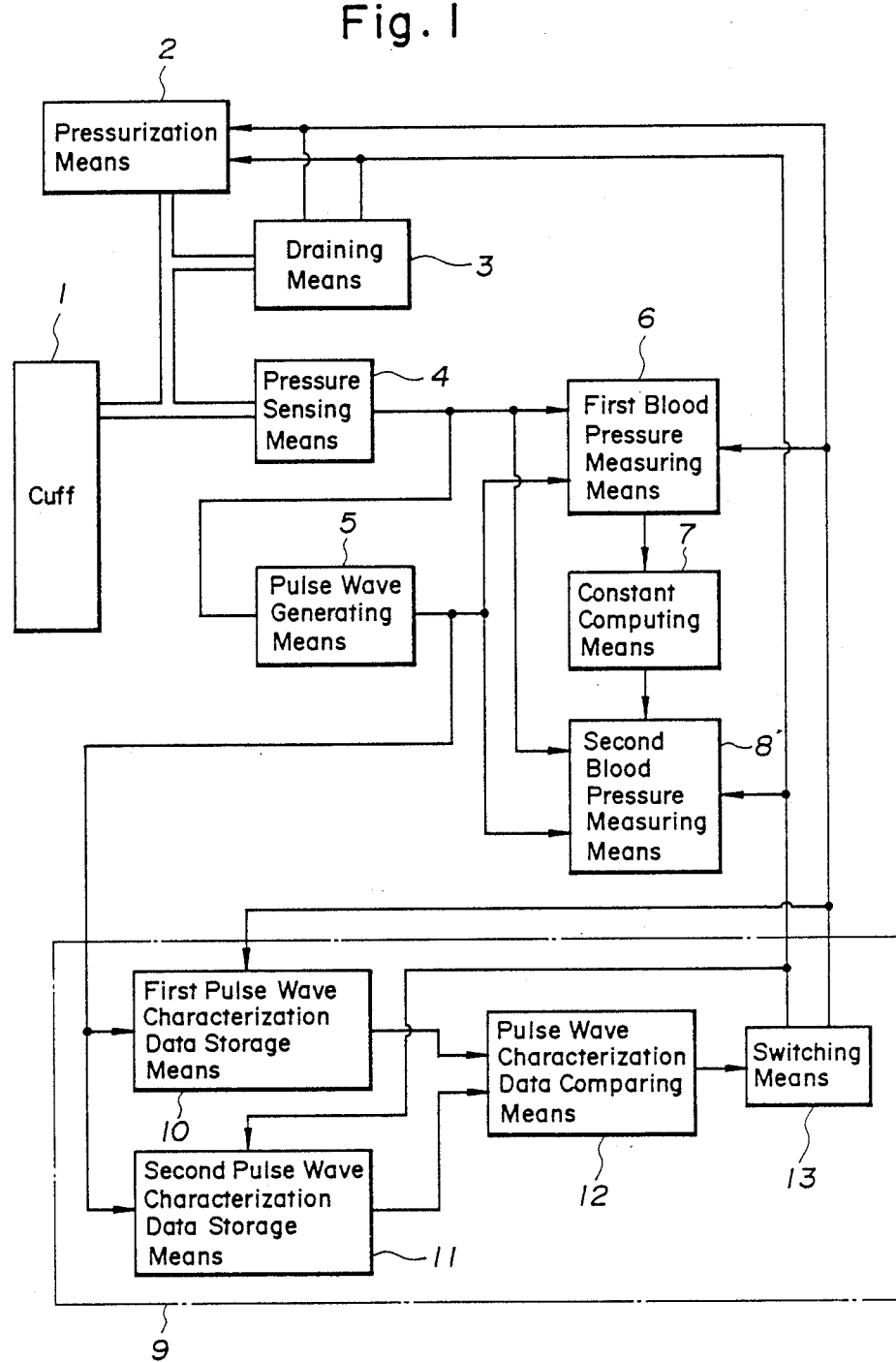
FIG. 1 is a schematic block diagram for explaining the main device claim of the present application relating to the electronic blood pressure measurement device of the present invention.
Figure 2:
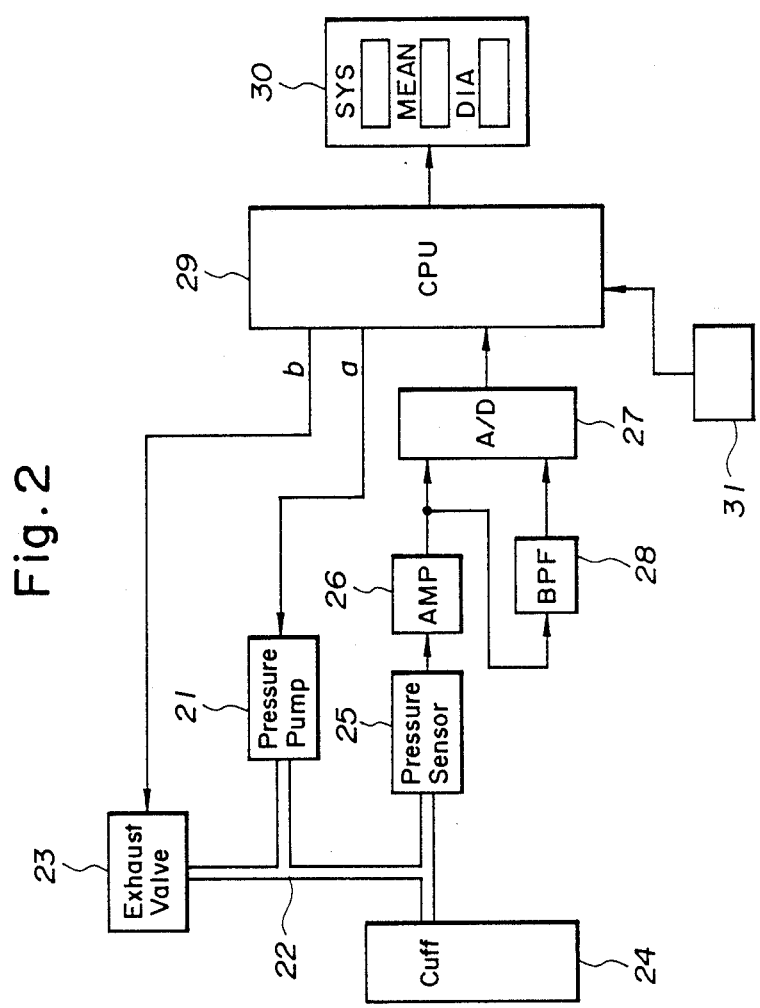
FIG. 2 is a schematic block diagram showing the overall construction of the preferred embodiment of the electronic blood pressure measurement device of the present invention, which performs the preferred embodiment of the blood pressure measurement device method of operation of the present invention.

The present invention will now be described with reference to the preferred embodiments of the device and of the method thereof, and with reference to the figures. In FIG. 2, there is shown a schematic overall block diagram of said preferred embodiment of the electronic blood pressure measurement device of the present invention. In this figure, the reference numeral 21 denotes a pressure pump, which is connected to an exhaust valve 23 and to a cuff 24 by way of an air conduit system 22. To the cuff 24 via the air conduit system 22 there is connected an air pressure sensor 25, and this air pressure sensor 25 outputs an electronic signal indicating the pressure level of the air in the cuff 24.

The output of the air pressure sensor 25 is fed to the input of an amplifier 26, the output of which on the one hand is directly connected to a first input side of an A/D converter 27, and on the other hand is connected to a second input side of said A/D converter 27 via a band pass filter 28. Thus, one of the input sides of said A/D converter 27 receives a static pressure value from the amplifier 26 representing the pressure in the cuff 24, while the other input side of said A/D converter 27 receives, via the band pass filter 28, a value representing the pulse wave component of said pressure in said cuff 24.

The output side of the A/D converter 27 is connected to an input of a CPU (central processing unit) 29 which typically is a microcomputer incorporating an microprocessor, and thereby digitalized data representing cuff pressure and the aforementioned pulse wave signal are fed to said CPU 29.

Within the CPU 29, there are provided various typical and per se conventional microcomputer components such as RAM (random access memory), ROM (read only memory), and so on; and this CPU performs the functions of determining values representing a systolic blood pressure, an average blood pressure, and a diastolic blood pressure, of the patient. Further, the CPU 29 performs the function of computing a constant A as being equal to (systolic blood pressure-average blood pressure) divided by (average blood pressure-diastolic blood pressure), the function of computing a systolic blood pressure from this computed constant A and the newly determined or current values of the average and the diastolic blood pressure, the function of computing constants $B_1$ and $B_2$ (pulse wave identification data) for comparing pulse wave forms, and the function of determining whether or not the ratio of $B_2$ to $B_1$ ($B_2/B_1$) is within a predetermined value range. These various calculations are performed by the CPU 29, based upon a program stored in its ROM, and keeping data values in its RAM.

Here, the constant $B_1$ is a constant which relates to the pulse wave form at the time when the constant A is computed, while the constant $B_2$ is a constant which relates to the pulse wave form at the time when a systolic blood pressure is determined using the constant A; i.e., $B=(P_{max}-P_{ave})/(P_{ave}-P_{min})$, where $P_{ave}$ is the average value, $P_{max}$ is the maximum value, and $P_{min}$ is the minimum value in one cycle of the pulse wave, as illustrated in the wave form diagram of FIG. 3.

The CPU 29 selectively outputs an electronic signal "a" so as to control the pressure pump 21, either to operate said pump 21 or to stop said pump 21; and, similarly, said CPU 29 selectively outputs an electronic signal "b" so as to control the exhaust valve 23, either to operate said exhaust valve 23 at a relatively high venting speed or to operate said exhaust valve 23 at a relatively low venting speedd. Further, the CPU 29 is internally equipped with a timer T1. The set time of the timer T1 is set on a digital switch 31.

According to the operation of this electronic blood pressure measurement device, as illustrated in the time chart of FIG. 4, in the first cycle of the timer T1 the CPU 29 determines values representing a systolic blood pressure, an average blood pressure, and a diastolic blood pressure of the patient. These determinations are performed via a sequential series of cuff pressure changes of pressurization, gradual venting, and rapid venting. This corresponds to blood pressure measurement by the first measuring means, according to the claims of the present patent application. Then the constant A is computed from these three blood pressure values, at time $t_1$ as shown in FIG. 4.

Thereafter, the sequential processed of pressurization, gradual venting, and rapid venting and elapsing of an interlude time are repeated every cycle T1, as shown in the time chart of FIG. 4, and each time, after determining an average blood pressure and a diastolic blood pressure, a systolic blood pressure is computed from said determined values of the average blood pressure and the diastolic blood pressure, and from the already determined constant A. This corresponds to measurement by the second measuring means according to the claims of the present patent application. The obtained three blood pressure values are displayed by the CPU on its display unit 30.

If it is determined that updating of the constant A is necessary, according to the values of the constants $B_1$ and $B_2$ when the systolic blood pressure is determined from the determined average and diastolic blood pressures and the constant A, then the processes of determining a systolic blood pressure, an average blood pressure, and a diastolic blood pressure are started anew (this corresponds to measurement by the second measuring means), so as to compute a new value of the constant F, thereby to update said constant A.

Now, the detailed action and operation of this preferred embodiment of the electronic blood pressure measurement device of the present invention, according to the preferred embodiment of the electronic blood pressure measurement device operating method of the present invention, will be described, with reference to the flow charts for fragments of the program obeyed by the CPU 29 incorporated therein shown in FIGS. 5, 6, and 7.

Figure 5:
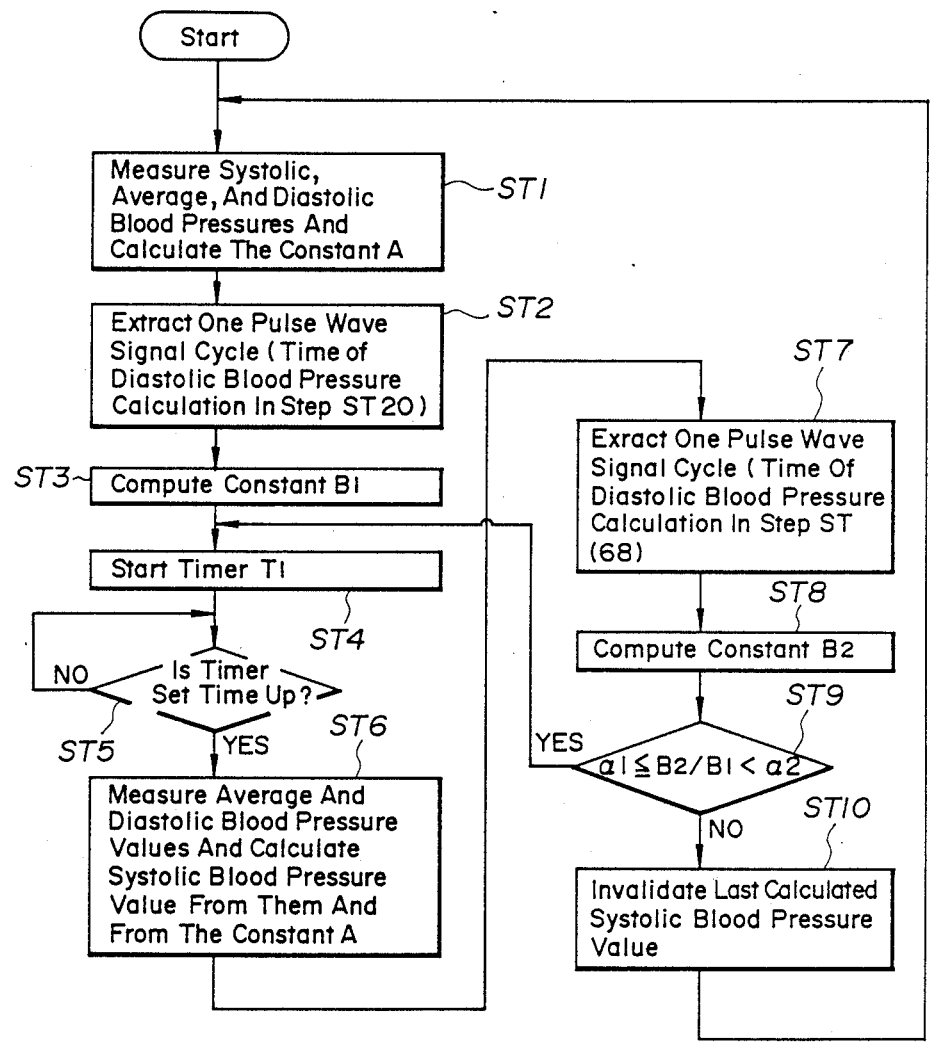
FIG. 5 is a flow chart illustrating the flow of a main fragment of a program which is stored in and obeyed by a microprocessor CPU incorporated in said preferred embodiment of the electronic blood pressure measurement device of the present invention.

Referring first to the main or overall flow chart shown in FIG. 5, when the action starts at the START box, first of all, in the step ST1, a systolic blood pressure, an average blood pressure, and a diastolic blood pressure are measured, and further the constant A is computed, and next the flow of control passes to the step ST2. In this step ST1, according to the present invention, any of a wide variety of per se known algorithms for computing such blood pressure values according to the oscillation method may be employed. Here, exemplarily and as is preferred, blood pressure values are computed according to the following guidelines:

systolic blood pressure: cuff pressure at which the increase rate of the pulse wave amplitude undergoes a relatively sharp increase.
average blood pressure: cuff pressure at which the amplitude of the pulse wave amplitude maximizes.
diastolic blood pressure: cuff pressure at which the decrease rate of the pulse wave amplitude undergoes a relatively sharp decrease.

Figure 6:
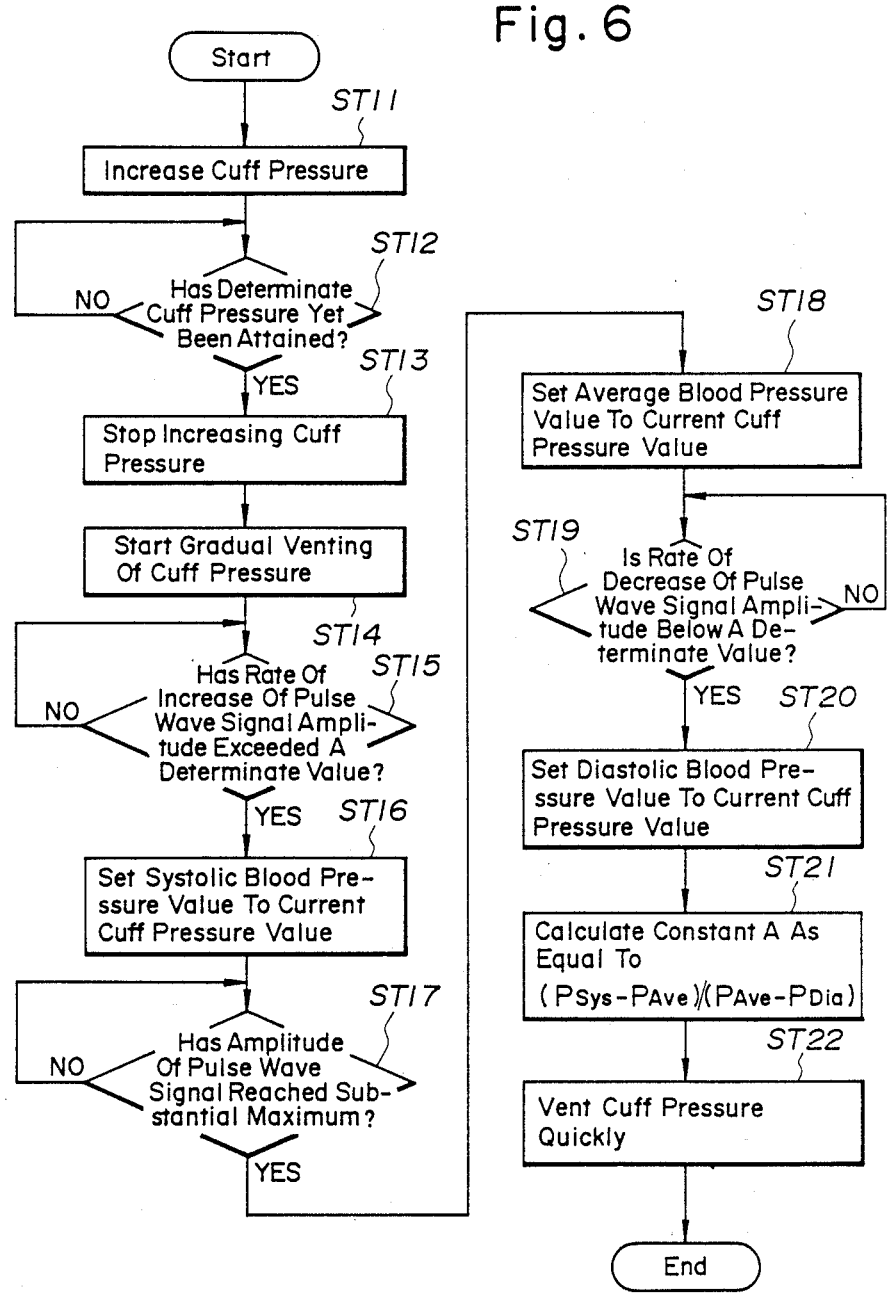
FIG. 6, similarly to FIG. 5, is a flow chart illustrating the flow of another program fragment stored in and obeyed by said microprocessor CPU, said program fragment being a routine included in the main program flow for measuring systolic, average, and diastolic blood pressure values and for computing a constant A.

In the flow chart of FIG. 6, there is shown the flow of another program fragment stored in and obeyed by the CPU 29, said program fragment incorporating the details of the above described determination of the systolic blood pressure, the average blood pressure, and the diastolic blood pressure, and of the computation of the constant A, and corresponding to this step ST1. This routine operates as follows.

After the start of the action in the START block, next, in the step ST11, the CPU 29 outputs an apropriate ON signal "a" to the pressure pump 21 to cause said pressure pump to operate so as to raise the pressure within the cuff 24 at a fairly rapid rate, thus to start inflating the cuff 24 and progressively squeezing the arm of the patient, which is passed through said cuff; and next the flow of control passes to the decision step ST12.

In this decision step ST12, each sample time, a decision is made as to whether the pressure in the cuff 24 has yet risen far enough to have attained a determinate pressure value, or not. This determinate pressure value is generally set to be greater than the maximum blood pressure that can occur in practice. If the answer to this decision is NO, so that the pressure in the cuff 24 is less than said dwterminate pressure value, then it is deemed that further cuff inflation is required, and then the flow of control passes back to this step ST12 again, to continue the inflation of the cuff 24. On the other hand, if the answer to this decision is YES, so that the pressure in the cuff 24 has now risen up to said determinate pressure value, then it is deemed that no further cuff inflation is currently required, and in this case the flow of control passes next to the step ST13.

In this step ST13, the inflation of the cuff is stopped, by the CPU 29 outputting an appropriate OFF signal "a" to the pressure pump 21 so as to cause said pressure pump to stop its operation; and next the flow of control passes to the step ST14.

In this step ST14, gradual venting of the air in the cuff 24 via the exhaust valve 23 is commenced, by the CPU 29 outputting an appropriate signal "b" to said exhaust valve 23, so that the cuff pressure starts steadily dropping; and next the flow of control passes to the decision step ST15.

In this decision step ST15, a decision is made as to whether the rate of increase of the amplitude of the pulse wave signal received by the CPU 29 has exceeded a determinate value, or not. If the answer to this decision is NO, so that in a sense the rate of increase of the amplitude of said pulse signal is substantially constant, then the flow of control passes again back to this step ST15 again, to loop repeatedly while meanwhile the cuff pressure gradually drops. On the other hand, if and when the answer to this decision is YES, so that now the rate of increase of the amplitude of the pulse wave signal received by the CPU 29 has exceeded the aforesaid determinate value, then the value of the cuff pressure at this point is suitable for being taken as being the value for the systolic blood pressure; and the flow of control passes next to the step ST16.

In this step ST16, the value for the cuff pressure at this time is stored in the RAM memory of the CPU 29 as the value of systolic blood pressure, and next the flow of control passes to the decision step ST17. Meanwhile, the cuff pressure continues to drop gradually and steadily according to the venting thereof through the exhaust valve 23. And at the same time the amplitude of the pulse wave increases.

In the decision step ST17, a decision is made as to whether the amplitude of said pulse wave signal has reached a substantially maximum value, or not. If the answer to this decision is NO, so that as yet the pulse wave signal amplitude is still substantially increasing, then it is deemed that more time should be allowed to elapse to allow said pulse wave signal amplitude to rise further, and thus the flow of control passes back to this step ST17 again, to loop repeatedly while meanwhile the pulse wave signal amplitude continues to rise. On the other hand, if the answer to this decision is YES, so that now the amplitude of said pulse wave signal has reached its substantially maximum value, then the flow of control passes next to the step ST18.

In this step ST18, the vaue of the cuff pressure at this point is taken as being the average blood pressure, and this value is stored in the RAM memory of the CPU 29 as said average blood pressure; and next the flow of control passes to the decision step ST19. Meanwhile, the cuff pressure further continues to drop gradually and steadily according to the venting thereof through the exhaust valve 23, while now at the same time the amplitude of the pulse wave decreases.

In this decision step ST19, a decision is made as to whether the rate of decrease of the amplitude of said pulse wave signal is smaller than a determinate value, or not. If the answer to this decision is NO, so that as yet the pulse wave signal amplitude is still decreasing at a substantially high speed, then it is deemed that more time should be allowed to elapse to allow said pulse wave signal amplitude further to drop at relatively high speed, and thus the flow of control passes back to this step ST19 again, to loop repeatedly while meanwhile the pulse wave signal amplitude continues to drop. On the other hand, if the answer to this decision is YES, so that now the rate of decrease of said pulse wave signal has dropped below said determinate value, then the flow of control passes next to the step ST20.

In this step ST20, the value of the cuff pressure at this point is taken as being the diastolic blood pressure, and this value is stored in the RAM memory of the CPU 29 as said diastolic blood pressure; and next the flow of control passes to the step ST21.

Now, the systolic blood pressure, the average blood pressure, and the diastolic blood pressure have been determined in this manner as described above. It should be understood that this process is per se conventional and is already known in the art of electronic blood pressure measurement devices.

Next, in the step ST21, the value of the constant A, which is defined as being equal to (systolic blood pressure-average blood pressure) divided by (average blood pressure-diastolic blood pressure), is calculated according to the thus above determined systolic blood pressure, average blood pressure, and diastolic blood pressure. And the computed value of said constant A is stored in the RAM memory of the CPU 29. Next, the flow of control passes to the step ST22.

In this step ST22, high speed venting of the air in the cuff 24 via the exhaust valve 23 is commenced, by the CPU 29 outputting an appropriate signal "b" to said exhaust valve 23, so that the cuff pressure starts steadily dropping; and next the flow of control passes to the end of this FIG. 6 routine, via the END block thereof.

By completion of the above FIG. 6 routine, the flow of control completes the action shown in FIG. 5 only by the block ST1, and next the flow of control passes to the step ST2. The explanation of FIG. 5 will now be recommenced. In this current step ST2, one cycle of the pulse wave signal is extracted, corresponding to the time at which the diastolic blood pressure was calculated in the step ST20. Then the flow of control passes to the next step ST3.

In this step ST3, the constant $B_1$ which specifies the pulse wave at this time point is calculated, according to $B_1 = (P_{max} - P_{ave})/(P_{ave} - P_{min})$. The average value $P_{ave}$ is calculated by the equation:

$$P_{ave} = \sum_{1}^{n} P(i)/(n+1)$$

where n is the number of data in one cycle, and P(i) is the A/D value of the pulse wave.

Following this calculation of the constant $B_1$, in the next step ST4 the timer T1 is started. Then the flow of control passes next to the decision step ST5.

In this decision step ST5, a decision is made as to whether the time counted by the timer (as set on the setting means 31 therefor) is up, or not; i.e., as to whether or not the time elapsed since the step ST4 has reached the set determinate value, or not. If the answer to this decision is NO, so that as yet the set determinate time has not elapsed, then the flow of control passes back to this step ST5 again, to execute a tight loop. On the other hand, if the answer to this decision is YES, so that now the set determinate time interval value has elapsed, then in this case the flow of control passes next to the step ST6. This delay loop step serves for suspending measurement of blood pressure, until the set time on the timer T1 has elapsed.

In the next step ST6, which is arrived at when the time as timed by the timer T1 has become equal to the aforesaid set value, first an average blood pressure and a diastolic blood pressure are determined, and then, based upon the ascertained values for these pressures and upon the value for the constant A determined in the step ST1, a systolic blood pressure is calculated. And, when this process is completed, then the flow of control passes to the step ST7.

Figure 7:
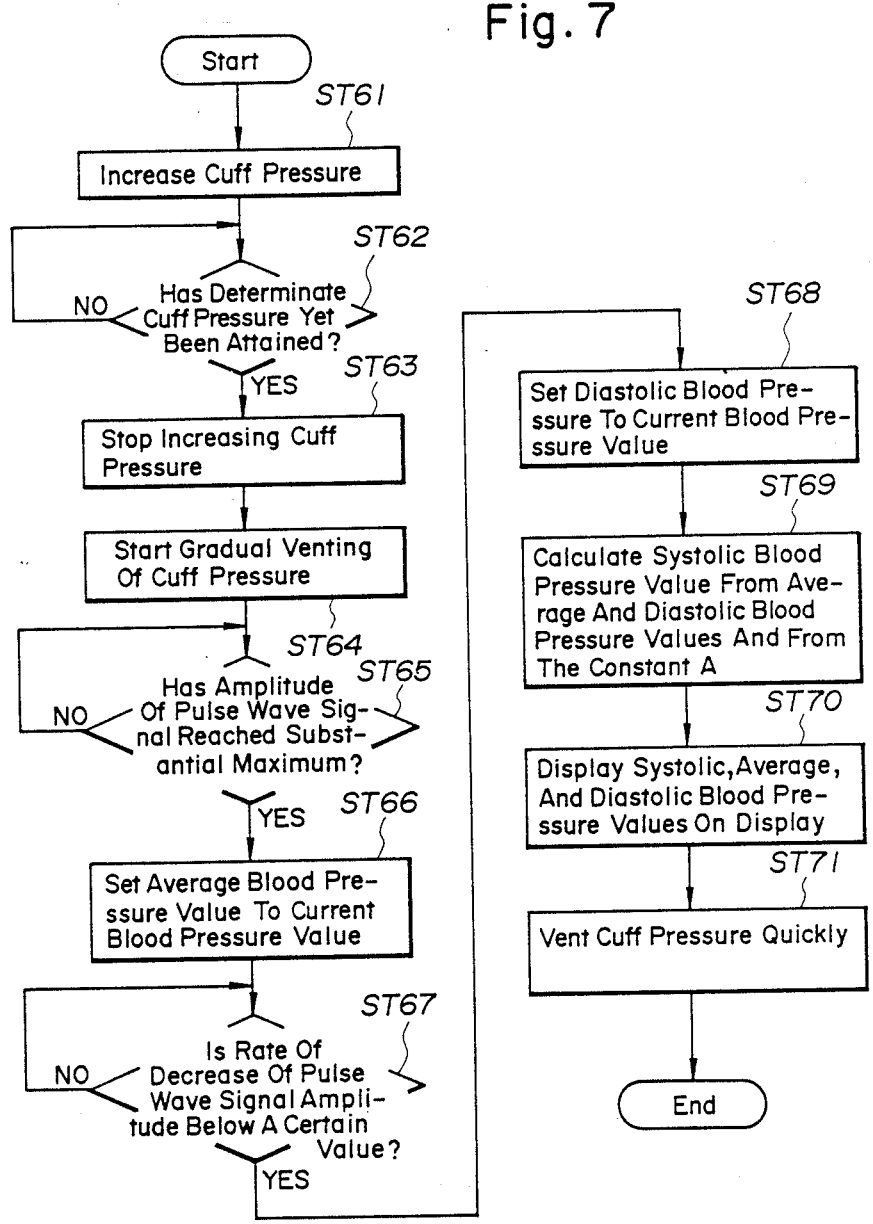
FIG. 7, similarly to FIGS. 5 and 6, is a flow chart illustrating the flow of yet another program fragment stored in and obeyed by said microprocessor CPU incorporated in the electronic blood pressure measurement device according to the preferred embodiment of the present invention, said program fragment being a routine included in the main program flow for determining the average blood pressure and the diastolic blood pressure and for computing the systolic blood pressure from them and from said constant A.

In the flow chart of FIG. 7, there is shown the flow of another program fragment stored in and obeyed by the CPU 29, and corresponding to this step ST6, said program fragment incorporating the details of the above described determination of the averaage blood pressure and the diastolic blood pressure, and then of the calculation of the systolic blood pressure therefrom based upon the value of the constant A as already previously determined in the step ST1. This routine operates as follows.

After the start of the action in the START block, next, in the step ST61, the CPU 29 outputs an appropriate ON signal "a" to the pressure pump 21 to cause said pressure pump to operate so as to raise the pressure within the cuff 24 at a fairly rapid rate, thus to start inflating the cuff 24 and progressively squeezing the arm of the patient, which is passed through said cuff; and next the flow of control passes to the decision step ST62.

In this decision step ST62, each sample time, a decision is made as to whether the pressure in the cuff 24 has yet risen far enough to have attained another certain determinate pressure value, or not. This determinate pressure value is, in this case, generally set to be only slightly greater than the average blood pressure; this is a difference between the processes of this FIG. 7 flow chart and the processes of the FIG. 6 flow chart. If the answer to this decision is NO, so that the pressure in the cuff 24 is less than said determinate pressure value, then it is deemed that further cuff inflation is required, and then the flow of control passes next back to this step ST62 again, to continue the inflation of the cuff 24. On the other hand, if the answer to this decision is YESA, so that the prssure in the cuff 24 has now risen up to said determinate pressure value, then it is deemed that no further cuff inflation is currently required, and in this case the flow of control passes next to the step ST63.

In this step ST63, the inflation of the cuff is stopped, by the CPU 29 outputting an appropriate OFF signal "a" to the pressure pump 21 so as to cause said pressure pump to stop its operation; and next the flow of control passes to the step ST64.

In this step ST64, gradual venting of the air in the cuff 24 via the exhaust valve 23 is commenced, by the CPU 29 outputting an appropriate signal "b" to said exhaust valve 23, so that the cuff pressure starts steadily and gradually dropping; and next the flow of control passes to the decision step ST65.

In this decision step ST65, a decision is made as to whether the amplitude of the pulse wave signal has reached a substantially maximum value, or not. If the answer to this decision is NO, so that as yet the pulse wave signal amplitude is still substantially increasing, then it is deemed that more time should be allowed to elapse to allow said pulse wave signal amplitude to rise further, and thus the flow of control passes back to this step ST65 again, to loop repeatedly while meanwhile the pulse wave signal amplitude continues to rise. On the other hand, if the answer to this decision is YES, so that now the amplitude of said pulse wave signal has reached its substantially maximum value, then the flow of control passes next to the step ST66.

In this step ST66, the value of the cuff pressure at this point is taken as being the average blood pressure, and this value is stored in the RAM memory of the CPU 29 as said average blood pressure; and next the flow of control passes to the decision step ST67. Meanwhile, the cuff pressure further continues to drop gradually and steadily according to the venting thereof through the exhaust valve 23, while at the same time the amplitude of the pulse wave decreases from this point of the process onwards.

In this decision step ST67, a decision is made as to whether the rate of decrease of the amplitude of said pulse wave signal is smaller than a determinate value, or not. If the answer to this decision is NO, so that as yet the pulse wave signal amplitude is still decreasing at a substantilly high speed, then it is deemed that more time should be allowed to elapse to allow said pulse wave signal amplitude further to drop at relatively high speed, and thus the flow of control passes back to this step ST67 again, to loop repeatedly while meanwhile the pulse wave signal amplitude continues to drop. On the other hand, if the answer to this decision is YES, so that now the rate of decrease of said pulse wave signal has dropped below said determinate value, then the flow of control passes next to the step ST68.

In this step ST68, the value of the cuff pressure at this point is taken as being the diastolic blood pressure, and this value is stored in the RAM memory of the CPU 29 as said diastolic blood pressure; and next the flow of control passes to the step ST69.

Now, the average blood pressure and the diastolic blood pressure have been determined in this manner as described above, similarly to what was done in the process of the FIG. 6 routine; but no value for the systolic blood pressure has yet been determined.

Next, in the step ST69, from the value of the constant A as determined previously in the FIG. 6 routine, and from the just above determined values for the average blood pressure and the diastolic blood pressure, a value for the systolic blood pressure is calculated as being equal to: average blood pressure+A(average blood pressure-diastolic blood pressure). And the computed value of said systolic blood pressure is stored in the RAM memory of the CPU 29. Next, the flow of control passes to the step ST70.

In this step ST70, the currently determined values for the systolic blood pressure, the average blood pressure, and the diastolic blood pressure are displayed on the display means 31 therefor; and next the flow of control passes to the step ST71.

In this step ST71, high speed venting of the air in the cuff 24 via the exhaust valve 23 is commenced, by the CPU 29 outputting an appropriate signal "b" to said exhaust valve 23, so that the cuff pressure starts steadily dropping; and next the flow of control passes to the end of this FIG. 7 routine, via the END block thereof.

By completion of the above FIG. 7 routine, the flow of control completes the action shown in FIG. 5 only by the block ST6, and next the flow of control passes to the step ST7. The explanation of FIG. 5 will now be recommenced. In this current step ST7, one cycle of the pulse wave signal is extracted, which was stored at the time at which the diastolic blood pressure was calculated in the step ST68. Then the flow of control passes to the next step ST8.

In the next step ST8, the constant $B_2$ which specifies the pulse wave signal at this time point is calculated, in the same way as the constant $B_1$ was calculated in the step ST3; and next the flow of control passes to the decision step ST9.

In this decision step ST9, a decision is made as to whether the ratio $B_1/B_2$ of the constants $B_1$ and $B_2$ is within a certain range defined as between set values $\alpha_1$ and $\alpha_2$, or not. For example, $\alpha_1$ may have the value 0.9 while $\alpha_2$ may have the value 1.1. If the answer to this decision is YES, so that the ratio $B_1/B_2$ of the constants $B_1$ and $B_2$ is in fact between the constants $\alpha_1$ and $\alpha_2$, then it is the case that the pulse wave form when measuring the blood pressure values in the step ST1 (as expanded in the FIG. 6 routine) and the pulse wave form when measuring the blood pressure values in the step ST6 (as expanded in the FIG. 7 routine) are basically similar to one another, i.e. no substantial change in the pulse wave form has occurred; and therefore it is deemed that no remeasurement of the systolic blood pressure and recalculation of the constant A are called for, so that next the flow of control is transferred to the step ST4, to restart the operation of the timer T1. On the other hand, if the answer to this decision is NO, so that so that the ratio $B_1/B_2$ of the constants $B_1$ and $B_2$ is in fact outside the range defined between the constants $\alpha_1$ and $\alpha_2$, then it is the case that the pulse wave form when measuring the blood pressure values in the step ST1 (as expanded in the FIG. 6 routine) and the pulse wave form when measuring the blood pressure values in the step ST6 (as expanded in the FIG. 7 routine) are substantially different from one another, i.e. a substantial change in the pulse wave form has now occurred, so that if merely the processes in the step ST6 were performed a substantial error in the determination of the systolic blood pressure would occur; and therefore it is deemed that direct remeasurement of the systolic blood pressure and subsequent recalculation of the constant A depending thereupon are called for, so that next the flow of control is transferred to the step ST10. In this final step ST10, the last value of the systolic blood pressure which was calculated is invalidated, and next the flow of control passes back to the step ST1.

Thus to recapitulate, in the event that the step ST1 is returned to when the test in the above explained decision step ST9 returns a NO result, the cuff pressure is initially raised higher than the anticipated systolic blood pressure value, and said cuff pressure is then subsequently gradually reduced, and during this process the systolid blood pressure, the average blood pressure, and the diastolic blood pressure are then again directly determined by observation of the characteristics of the pulse wave signal, and a new updated value for the constant A is computed based upon these new values for the systolic blood pressure, the average blood pressure, and the diastolic blood pressure. Also, the constant $B_1$ is computed. Thereafter, as the loop from the step ST4 to the step ST10 is traversed again and again at time intervals according to the set timing of the timer T1, as long as the test in the above explained decision step ST9 returns a YES result, the constant $B_2$ is repeatedly recomputed, and only the average blood pressure and the diastolic blood pressure are directly measured, by raising the cuff pressure to be only slightly higher than the expected value for said average blood pressure, while the systolic blood pressure is derived by calculation from said values for the average blood pressure and for the diastolic blood pressure, as well as from the value of the constant A previously computed. This loop continues to be executed until the ratio $B_1/B_2$ of the constants $B_1$ and $B_2$ comes no longer to be between the set values $\alpha_1$ and $\alpha_2$, and in such a case the systolic blood pressure value and the constant A are updated again.

It will therefore be seen that, considering the operation of this device and the operational method therefor as specified above from the point of view of the language of the claims, since when the blood pressure wave form does not substantially change there is no substantial change in the pulse wave form, therefore at this time the comparison of the first and said second stored pulse wave characterization data (the constants $B_1$ and $B_2$) produces the result that they are not more distinguished from one another than the set determinate standard (determined by their ratio in the shown preferred embodiments), and therefore the steps of operating the second blood pressure measuring means and of computing the systolic blood pressure from the thereby measured average blood pressure and the diastolic blood pressure and from the value of the constant A are repeated, without unduly squeezing the patient's arm; but the value of the constant is not updated. On the other hand, when a significant change occurs in the blood pressure wave form, a corresponding substantial change occurs in the pulse wave form, and therefore at this time the comparison of the first and said second stored pulse wave characterization data produces the result that they are now definitely more distinguished from one another than said determinate standard, and therefore the step of operating the first blood pressure determining means and of directly measuring the systolic blood pressure as well as the average blood pressure and the diastolic blood pressure is once repeated, thereby unavoidably once relatively severely squeezing the patient's arm. And then the constant A is again updated from these new blood pressure measurements, and then the cycle of repeatedly operating the second blood pressure measuring means are again commenced. Hence, in summary, it is seen that the patient's arm is squeezed to a relatively severe amount, when and only when such severe squeezing is absolutely necessary in order to achieve proper blood pressure measurement.

Although the present invention has been shown and described in terms of the preferred embodiment thereof, and with reference to the appended drawings, it should not be considered as being particularly limited thereby, since the details of any particular embodiment, or of the drawings, could be varied without, in many cases, departing from the ambit of the present invention. For example, although in the above described preferred embodiment of the present invention the test as to whether or not remeasurement of the systolic blood pressure and recalculation of the constant A are required is performed based upon whether or not the ratio $B_1/B_2$ of the constants $B_1$ and $B_2$ determined as explained hereinabove is or is not between the set values $\alpha_1$ and $\alpha_2$, this is not the only possibility for the present invention. It would be possible to decide whether or not the relevant pulse waves are similar based upon other wave form comparison techniques, such as for example comparing the absolute value of the difference between the constants $B_1$ and $B_2$ with some other determinate value. Other possibilities could also be conceived of. Accordingly, the scope of the present invention is to be considered as being delimited, not by any particular perhaps entirely fortuitous details of the disclosed preferred embodiment, or of the drawings, but solely by the scope of the accompanying claims, which follow.

What is claimed is:

1. An electronic blood pressure measurement device, comprising:
   (a) a cuff for being fitted around the arm of a patient;
   (b) a means for selectively pressurizing said cuff with fluid, so as to squeeze said arm of said patient;
   (c) a means for selectively draining said fluid from said cuff either at a relatively rapid rate or at a relatively slow rate;
   (d) a means for sensing the pressure of said fluid in said cuff and for producing an output signal representative thereof;
   (e) a means for receiving said pressure signal from said cuff pressure sensing means and for generating therefrom a signal representative of the pulse wave of the patient;
   (f) a first blood pressure measuring means for determining for the patient a systolic blood pressure, an average blood pressure, and a diastolic blood pressure according to said pulse wave signal, during the course of pressurization and gradual evacuation at said relatively slow rate of said cuff;
   (g) a means for computing the value of a constant as being the ratio of the difference of said systolic blood pressure and said average blood pressure to the difference of said average blood pressure and said diastolic blood pressure, all said blood pressures being as determined by said first blood pressure measuring means;
   (h) a second blood pressure measuring means for determining for the patient an average blood pressure and a diastolic blood pressure according to said pulse wave signal, during the course of gradual evacuation at said relatively slow rate of said cuff;
   (i) a means for computing the value of a systolic blood pressure, according to said average blood pressure and said diastolic blood pressure as determined by said second blood pressure measuring means, and according to the value of said constant as computed by said computing means therefor; and (j) a control means which comprises first and second means for storing pulse wave characterization data, means for comparing said pulse wave characterization data, and switching means for selectively actuating the means for selectively pressurizing, the means for selectively draining, the first and second blood pressure measuring means, and the means for computing the value of the constant and the value of the systolic blood pressure, and wherein the control means comprises means for:

(j1) operating, via said switching means, said first blood pressure measuring means so as to determine for the patient a systolic blood pressure, an average blood pressure, and a diastolic blood pressure according to the current pulse wave signal;

(j2) operating, via said switching means, said constant value computing means so as to determine the value of said constant as being the ratio of the difference of said systolic blood pressure and said average blood pressure to the difference of said average blood pressure and said diastolic blood pressure, all said blood pressures being as determined by said first blood pressure measuring means; and operating said first means for storing pulse wave characterization data to store pulse wave characterization data relating to the pulse wave at this time; and (j3) thereafter, repeatedly performing the following steps:

(i) operating, via said switching means, said second blood pressure measuring means for determining for the patient an average blood pressure and a diastolic blood pressure according to said pulse wave signal;

(ii) operating, via said switching means, said means for computing the value of a systolic blood pressure, according to said average blood pressure and said diastolic blood pressure as determined by said second blood pressure measuring means, and according to the value of said constant as computed by said computing means; and operating said second means for storing pulse wave characterization data to store pulse wave characterization data relating to the pulse wave at this time; and (iii) operating said means for comparing said pulse wave characterization data to compare the pulse wave characterization data stored in said first and said second means for storing pulse wave characterization data; and, if the result of said comparison indicates that said pulse wave characterization data stored in said first storage means are dissimilar from said pulse wave characterization data stored in said second storage means, then operating, via said switching means, said first blood pressure measuring means so as to determine for the patient a systolic blood pressure, an average blood pressure, and a diastolic blood pressure according to the present pulse wave signal.

2. A method for operating an electronic blood pressure measurement device, comprising the steps of:

(a) providing a cuff for being fitted around the arm of a patient;

(b) providing a means for selectively pressurizing said cuff with fluid, so as to squeeze said arm of said patient;

(c) providing a means for selectively draining said fluid from said cuff either at a relatively rapid rate or at a relatively slow rate;

(d) providing a means for sensing the pressure of said fluid in said cuff and for producing an output signal representative thereof;

(e) providing a means for receiving said pressure signal from said cuff pressure sensing means and for generating therefrom a signal representative of the pulse wave of the patient;

(f) providing a first blood pressure measuring means for determining for the patient a systolic blood pressure, an average blood pressure, and a diastolic blood pressure according to said pulse wave signal, during the course of pressurization and gradual evacuation at said relatively slow rate of said cuff;

(g) providing a second blood pressure measuring means for determining for the patient an average blood pressure and a diastolic blood pressure according to said pulse wave signal, during the course of gradual evacuation at said relatively slow rate of said cuff, wherein the following steps are further performed:

(1) operating said first blood pressure measuring means so as to determine for the patient a systolic blood pressure, an average blood pressure, and a diastolic blood pressure according to the present pulse wave signal;

(2) determining a value of a constant as being the ratio of the difference of said systolic blood pressure and said average blood pressure to the difference of said average blood pressure and said diastolic blood pressure, all said blood pressures being as determined by said first blood pressure measuring means; and first pulse wave characterization data relating to the pulse wave at this time are stored; and (3) thereafter, repeatedly performing the following steps:

(i) operating said second blood pressure measuring means for determining for the patient an average blood pressure and a diastolic blood pressure according to said pulse wave signal;

(ii) computing a systolic blood pressure according to said average blood pressure and said diastolic blood pressure as determined by said second blood pressure measuring means, and according to the value of said constant as determined; and second pulse wave characterization data relating to the pulse wave at this time are stored; and (iii) comparing said first said second stored pulse wave characterization data; and if the result of said step of comparing indicates that said first stored pulse wave characterization data are dissimilar from said second pulse wave characterization data, then operating, via said switching means, said first blood pressure measuring means so as to determine for the patient a systolic blood pressure, an average blood pressure, and a diastolic blood pressure according to the present pulse wave signal.

3. An electronic blood pressure measurement device, comprising:
a cuff;

means for pressuring said cuff;

means for selectively draining the pressure in said cuff either at a relatively rapid rate or at a relatively slow rate;

means for sensing said pressure in said cuff;

means for detecting a pulse wave signal in said cuff pressure;

first blood pressure measurement means for determining a systolic pressure, an average blood pressure, and a diastolic blood pressure according to said pulse wave information detected in said pulse wave signal detecting means and an output of said pressure sensing means, during the course of gradual evacuation at said relatively slow rate of said cuff;

means for computing the value of a constant as being the ratio of the difference of said systolic blood pressure and said average blood pressure to the difference of said average blood pressure and said diastolic blood pressure, each of said systolic, average and diastolic blood pressures having been determined by said first blood pressure measurement means;

second blood pressure measurement means for computing the value of a systolic blood pressure, according to said average blood pressure and said diastolic pressure as determined by an average blood pressure and diastolic blood pressure on the basis of a pulse wave information detected by a pulse wave signal detecting means and an output of a pressure sensing means, during the course of gradual evacuation at a relatively slow rate of said cuff, and according to said constant computed by said computing means; and measurement control means for repeatedly at time intervals performing the measurement by said first blood pressure means at a first stage and the measurement by said second blood pressure measuring means at a second stage after said first stage, wherein said measurement control means comprises means for storing a first pulse wave form data at said first stage, means for storing a second pulse wave form data at said second stage, and means for making a comparison between said first pulse wave form data and said second pulse wave form data.

4. The electronic blood pressure measurement device as defined in claim 3, wherein said first pulse wave form storing means stores a pulse wave characteristic data detected by said pulse wave signal detecting means at measuring said diastolic blood pressure in said first stage.

5. The electronic blood pressure measurement device as defined in claim 3, wherein said second pulse wave form storing means stores a pulse wave characteristic data detected by said pulse wave signal detecting means at measuring said diastolic blood pressure in said second stage.

6. The electronic blood pressure measurement device as defined in claim 3, wherein said measurement control means is provided with switching means for repeatedly making measurements by said second blood pressure measurement means in said second stage as long as said two pulse waves forms being compared are similar within a certain determined degree and for making the measurement by said first blood pressure means in said first stage when said two pulse wave forms being compared become no longer similar within said certain determined degree.

* * * * *